US007947257B2

(12) United States Patent
Watts et al.

(10) Patent No.: US 7,947,257 B2
(45) Date of Patent: May 24, 2011

(54) METHOD OF INTRANASAL ADMINISTRATION OF GRANISETRON

(75) Inventors: Peter James Watts, Nottingham (GB); Alan Smith, Nottingham (GB); Jonathan Castile, Nottingham (GB)

(73) Assignee: Archimedes Development Limited, Nottingham (GB)

( * ) Notice: Subject to any disclaimer, the term of this patent is extended or adjusted under 35 U.S.C. 154(b) by 0 days.

(21) Appl. No.: 11/004,556

(22) Filed: Dec. 3, 2004

(65) Prior Publication Data

US 2005/0142073 A1 Jun. 30, 2005

(30) Foreign Application Priority Data

Dec. 5, 2003 (GB) .................................. 0328186.2

(51) Int. Cl.
*A61K 9/08* (2006.01)
*A61K 9/12* (2006.01)
(52) U.S. Cl. ........................... 424/45; 424/434; 424/493
(58) Field of Classification Search .................... 424/45, 424/434, 493
See application file for complete search history.

(56) References Cited

U.S. PATENT DOCUMENTS

| 5,655,517 A | 8/1997 | Coffee | |
|---|---|---|---|
| 5,897,858 A * | 4/1999 | Haslwanter et al. | 424/78.04 |
| 5,929,059 A | 7/1999 | Sanger et al. | |
| 5,952,340 A | 9/1999 | Sanger et al. | |
| 2002/0132803 A1 * | 9/2002 | Dedhiya et al. | 514/182 |

FOREIGN PATENT DOCUMENTS

| CN | 1452964 A | 11/2003 |
|---|---|---|
| CN | 1452965 A | 11/2003 |
| EP | 0 376 385 A2 | 7/1990 |
| EP | 0 470 872 A1 | 2/1992 |
| EP | 1 250 925 A2 | 10/2002 |
| WO | 95/28158 A1 | 10/1995 |
| WO | WO 96/03142 A1 | 2/1996 |
| WO | WO 98/30207 A1 | 7/1998 |
| WO | WO 99/01498 A1 | 1/1999 |
| WO | WO 03080021 * | 10/2003 |
| WO | 2005060945 A2 | 7/2005 |

OTHER PUBLICATIONS

"Therapeutic Drugs", *Dollery (ed)*, 2nd edition, pp. G86-G90, (1999).
"The Complete Drug Reference", *Martindale*, 33rd Edition Pharmaceutical Press, pp. 1227-1228, (2002).
Illum, "Nasal drug delivery: new developments and strategies", *Drug Discovery Today*, vol. 7, No. 23, pp. 1184-1189, (2002).
Lipincott, "Remington: The Science and Practice of Pharmacy", 20th Edition, Chapter 37, pp. 681-699 (2000).
J.T. Carstensen, "Pharmaceutical Priciples of Solid Dosage Forms", Chapter 6, pp. 95-105, (1993).
A.T. Florence et al., "Physicochemical Principles of Pharmacy", 3rd Edition, pp. 357-360, (1998).

A. Martin, "Physical Pharmacy", *Physical Chemical Principles in the Pharmaceutical Sciences*, 4th Edition, pp. 516-519, (1993).
"Physician Desk Reference", 57 Edition, (2003).
Anonymous, "Kytril (granisetron hydrochloride) Injection", www.rocheusa.com, pp. 1-3 (Aug. 2002).
Anonymous, "Kytril (granisetron hydrochloride) Injection", www.rocheusa.com, pp. 1-3 (Jun. 2001).
Kraut, L., et al., "Anti-Emetics for Cancer Chemotherapy-Induced Emesis: Potential of Alternative Delivery Systems", *Drugs*, vol. 61, No. 11, pp. 1553-1562 (2001).
Aspden, T., et al, "Chitosan as a Nasal Delivery System: The Effect of Chitosan Solutions on in Vitro and in Vivo Mucociliary Transport Rates in Human Turbinates and Volunteers", *J. Pharm. Sciences*, vol. 86, No. 4, pp. 509-513 (pp. 509-513) (Apr. 1997).
"Granisetron," from Wikipedia, the free encyclopedia, (http://en.wikipedia.org/wiki/Granisetron) Feb. 20, 2007 printout, 2 pages.
Illum, L., et al., "Novel chitosan-based delivery systems for the nasal administration of a LHRH-analogue," S.T.P. Pharma Sciences, 2000, vol. 10, 89-94 (1).
Hinchcliffe, Michael, et al. "Effect of chitosan on teh intranasal absorption of salmon calcitonin in sheep," JPP 2005, 57:681-687.
L. Illum et al. "Intranasal Delivery of Morphine," The Journal of Pharmacology and Experimental Therapeutics, 2002, vol. 301, No. 1, pp. 391-400.
International Preliminary Report on Patentability dated Jun. 7, 2006, with Written Opinion and International Search Report, 12 pages.
Official Action in Indian Application No. 643/MUMNP/2006, dated Apr. 23, 2009, 3 pages.
Official Action in Mexican Application No. PA/a/2006/006239, dated Feb. 16, 2009, 3 pages.
Official Action in Mexican Application No. PA/a/2006/00629, dated May 14, 2009, 3 pages.
Official Action in Mexican Application No. PA/a/2006/00629, dated Jul. 27, 2009, 3 pages.
Official Action in Israeli Application No. 176132, dated Mar. 19, 2009, 2 pages.
Official Action in Israeli Application No. 176132, dated Jun. 25, 2009, 2 pages.
Official Action in Israeli Application No. 176132, dated Sep. 24, 2009, 3 pages.
Official Action in Chinese Application No. 2004800398583, dated Jul. 30, 2008, 9 pages.
Examination Report in New Zealand Application No. 547848, dated Jan. 30, 2008, 1 page.
Examination Report in New Zealand Application No. 547848, dated Nov. 18, 2008, 1 page.
Examination Report and Notice of Acceptance of Complete Specification in New Zealand Application No. 547848, dated Apr. 16, 2009.
Letters Patent issued Aug. 13, 2009 for New Zealand Application No. 547848, 1 page.
Certificate of Grant of Patent for Singapore Application No. 200603779-0, 1 page.

(Continued)

*Primary Examiner* — Mina Haghighatian
(74) *Attorney, Agent, or Firm* — Panitch Schwarze Belisario & Nadel LLP

(57) ABSTRACT

Compositions are provided for the intranasal administration of granisetron or a pharmaceutically acceptable salt thereof. Preferred compositions are in the form of an aqueous solution. Optionally, the compositions comprise chitosan, a salt or derivative thereof or a salt of a derivative of chitosan. The compositions can be used for the treatment or prevention of nausea and/or vomiting.

24 Claims, 1 Drawing Sheet

OTHER PUBLICATIONS

Communication under Rule 71(3) EPC for European Application No. 04 798 713.6, dated Jan. 28, 2009, with attached amended application as allowed, 27 pages.

Illum, Lisbeth, et al. "Chitosan as a Novel Nasal Delivery System for Peptide Drugs," Pharmaceutical Research, vol. 11, No. 8, (1994) pp. 1186-1189.

Examination Report in Australian Patent Application No. 2004296586 dated Apr. 21, 2010, 2 pages.

Decision on Rejection in Chinese Patent Application No. 200480039858.3, dated Jan. 22, 2010, 11 pages.

* cited by examiner

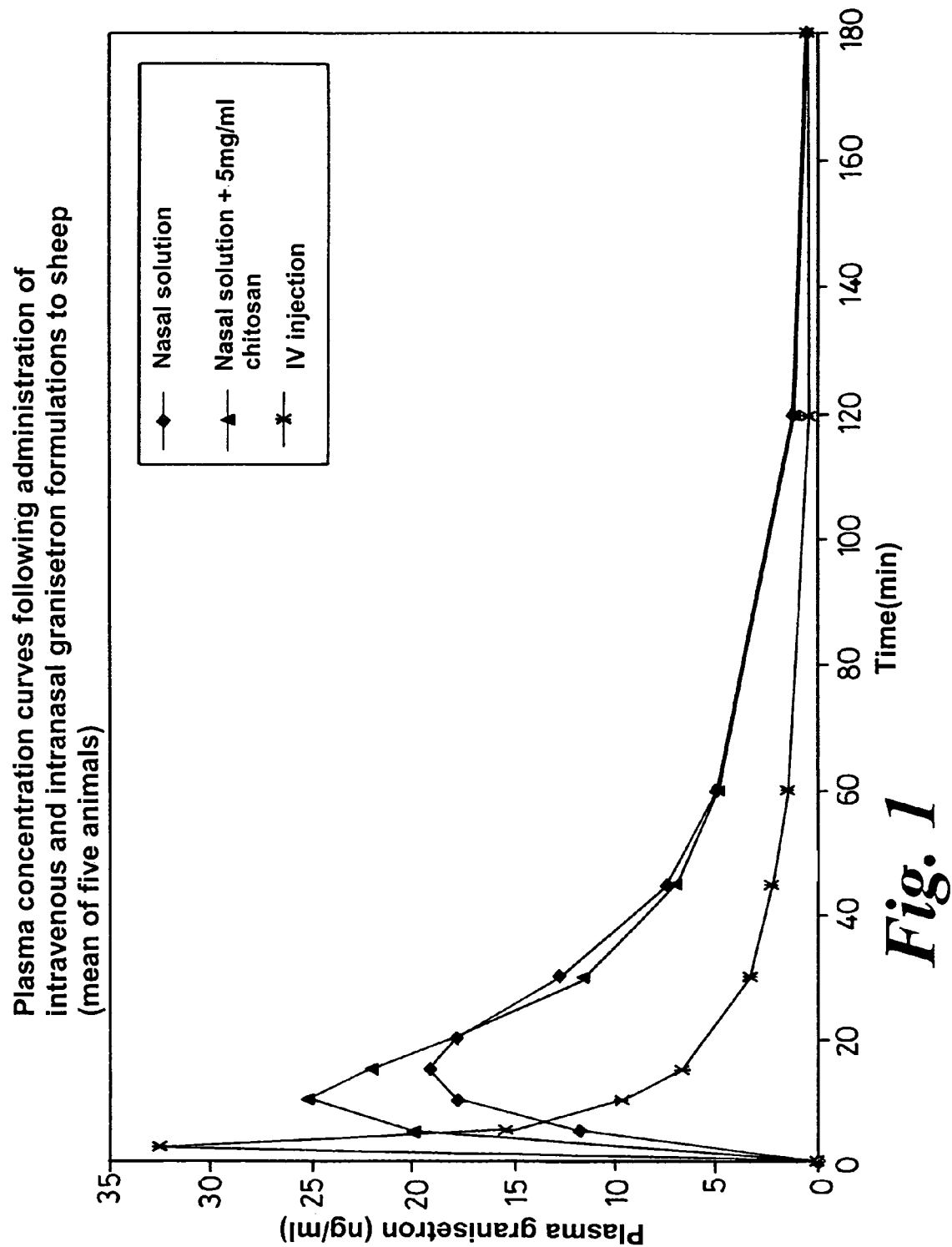

METHOD OF INTRANASAL ADMINISTRATION OF GRANISETRON

BACKGROUND OF THE INVENTION

This invention relates to pharmaceutical compositions for the intranasal administration of the compound granisetron and its pharmaceutically acceptable salts.

Granisetron (molecular weight 312.4) is 1-methyl-N-(9-methyl-9-azabicyclo[3.3.1]non-3-yl)-1H-indazole-3-carboxamide and has the following structure.

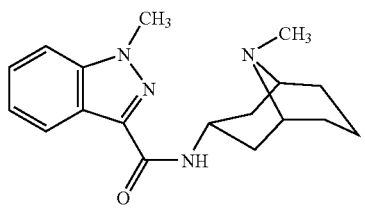

Granisetron is an antagonist of serotonin type 5-$HT_3$ receptors and has anti-emetic activity. It is thought that granisetron acts by binding to receptors in the chemoreceptor trigger zone and, probably, the upper gastrointestinal tract (see pages G86-G90, *Therapeutic Drugs*, Dollery (ed), $2^{nd}$ edition, Churchill Livingstone, Edinburgh, (1999)).

Granisetron is typically administered therapeutically as the hydrochloride salt (MW 348.9), but doses are usually expressed in terms of the base (1 mg base is equivalent to 1.12 mg of hydrochloride salt).

For treating nausea and vomiting induced by cytotoxic chemotherapy or radiotherapy, the typical adult oral dose is 1 to 2 mg up to one hour before therapy begins, then 2 mg daily in 1 or 2 divided doses. By intravenous injection, the dose is in the USA 10 µg/kg in both adults and children. For prevention or treatment of postoperative nausea and vomiting in adults, a 1 mg dose is given by intravenous infusion (max. dose 2 mg in one day) (Martindale, *The Complete Drug Reference*, $33^{rd}$ Edition, Pharmaceutical Press, pages 1227 and 1228 (2002)).

Both nausea and vomiting impair the absorption of orally administered drugs. It would be advantageous to provide granisetron for administration via a route that avoids the problems associated with oral drug administration. The present invention seeks to address this problem.

BRIEF SUMMARY OF THE INVENTION

The present inventors have found that the intranasal route of administration can be advantageous for granisetron and can offer significant benefits compared with administration via the oral route. In particular, it has been found that the intranasal route of administration can be advantageous in the treatment or prevention of nausea and/or vomiting.

The present invention provides a composition for nasal delivery comprising granisetron or a pharmaceutically acceptable salt thereof.

Granisetron may be used as the free base or in the form of a pharmaceutically acceptable salt. Suitable pharmaceutically acceptable salts include, but are not limited to, the hydrochloride, mesilate, citrate, nitrate, lactate, maleate, tartrate, phosphate, succinate, fumarate and gluconate salts. Preferably granisetron hydrochloride is used.

When producing a composition containing a salt of granisetron, the appropriate salt may be used or granisetron base may be dissolved in situ in a suitable acid.

The composition may be in any form suitable for nasal delivery. Suitable forms include aqueous or non-aqueous solutions and powders.

BRIEF DESCRIPTION OF THE SEVERAL VIEWS OF THE DRAWINGS

The foregoing summary, as well as the following detailed description of the invention, will be better understood when read in conjunction with the appended drawing. For the purpose of illustrating the invention, there is shown in the drawing one embodiment. It should be understood, however, that the invention is not limited to the precise arrangements and instrumentalities shown. In the drawings:

FIG. 1 is a graph showing comparative plasma concentration curves over time following administration of intravenous and intranasal granisetron formulations to sheep.

DETAILED DESCRIPTION OF THE INVENTION

In one aspect, the present invention provides an aqueous solution comprising granisetron or a pharmaceutically acceptable salt thereof, which is suitable for nasal delivery.

The aqueous solutions of the present invention preferably comprise granisetron or a pharmaceutically acceptable salt thereof in a concentration of about 0.2 to 150 mg/ml (expressed as the free base) (for example about 1 to 150 mg/ml), more preferably about 0.5 to 125 mg/ml (for example about 2 to 125 mg/ml) and most preferably about 1 to 100 mg/ml (for example about 5 to 100 mg/ml). Hence, when granisetron is used in the form of the hydrochloride salt, the concentration of granisetron hydrochloride is preferably about 0.22 to 168 mg/ml (for example about 1.1 to 168 mg/ml), more preferably about 0.56 to 140 mg/ml (for example about 2 to 140 mg/ml) and most preferably about 1.12 to 112 mg/ml (for example about 6 to 112 mg/ml).

The viscosity of the aqueous solutions of the present invention is preferably less than about 250 centipoise (cp), more preferably less than about 200 cp and most preferably less than about 150 cp.

The aqueous solutions of the present invention are preferably isotonic or close to isotonic. The osmolality of the solutions is preferably about 0.15 to 0.45 osmol/kg, more preferably about 0.20 to 0.40 osmol/kg and most preferably about 0.25 to 0.35 osmol/kg, for example about 0.29 osmol/kg.

The osmolality of the aqueous solutions may be adjusted to the desired value by the addition of any suitable osmolality adjusting agents known in the art. Agents that may be used to adjust the osmolality include, but are not limited to, polyols such as mannitol or sorbitol, sugars such as dextrose or salts such as sodium chloride. The preferred agents for adjusting the osmolality of the aqueous solutions are sodium chloride and mannitol. These agents may be used alone or in combination.

The aqueous solutions of the invention preferably have a pH of about 3 to 8, more preferably about 3.5 to 7.5 and most preferably about 4.0 to 7.0. The pH of the solutions may be adjusted to the desired value using any suitable organic or inorganic acid or organic or inorganic base. Suitable organic acids include, but are not limited to, acetic acid, citric acid, glutamic acid and methane sulfonic acid. Suitable inorganic acids include, but are not limited to, hydrochloric acid and sulphuric acid. Suitable organic bases include, but are not limited to, meglumine, lysine and tromethamine (TRIS).

Suitable inorganic bases include, but are not limited to, sodium hydroxide and potassium hydroxide. Alternatively, or in addition, a buffer system may be included in the compositions in order to adjust and maintain pH. Examples of suitable buffer systems include, but are not limited to, sodium dihydrogen phosphate/potassium hydrogen phosphate, sodium citrate/citric acid and citric acid/sodium phosphate.

The aqueous solutions of the invention may additionally comprise chitosan, a salt or derivative of chitosan or salt of a derivative of chitosan.

Chitosan is a cationic biopolymer comprising glucosamine and N-acetyl glucosamine that has bioadhesive properties and has been shown to improve the systemic bioavailability of certain drug compounds across mucosal surfaces, such as the nasal cavity (see Illum, *Drug Discovery Today*, 7:1184-1189 (2002)).

By the term "chitosan" we include all derivatives of chitin, or poly-N-acetyl-D-glucosamine, including all polyglucosamines and oligomers of glucosamine materials of different molecular weights, in which the greater proportion of the N-acetyl groups have been removed through hydrolysis (deacetylation). In accordance with the present invention, the degree of deacetylation, which represents the proportion of N-acetyl groups which have been removed through deacetylation, should preferably be in the range of about 40-97%, more preferably in the range of about 60-96% and most preferably be in the range of about 70-95%.

The chitosan, chitosan derivative or salt used in the present invention should preferably have a molecular weight in the range of about 10,000 to 1,000,000 Da, more preferably in the range of about 15,000 to 750,000 Da and most preferably in the range of about 20,000 to 500,000 Da.

Salts of chitosan are suitable for use in the present invention. Salts with various organic and inorganic acids are suitable. Such suitable salts include, but are not limited to, the nitrate, phosphate, glutamate, lactate, citrate, hydrochloride and acetate salts. Preferred salts are the hydrochloric acid and glutamic acid salts.

Chitosan derivatives and their salts are also suitable for use in this invention. Suitable chitosan derivatives include, but are not limited to, esters, ethers or other derivatives formed by bonding acyl and/or alkyl groups with the hydroxyl groups, but not the amino groups of chitosan. Examples include O-alkyl ethers of chitosan and O-acyl esters of chitosan. Modified chitosans, such as those conjugated to polyethylene glycol may be used in the present invention. Conjugates of chitosan and polyethylene glycol are described in International patent application publication WO99/01498.

Chitosans suitable for use in the present invention may be obtained form various sources, including Primex, Haugesund, Norway; NovaMatrix, Drammen, Norway; Seigagaku America Inc., MD, USA; Meron (India) Pvt, Ltd., India; Vanson Ltd, VA, USA; and AMS Biotechnology Ltd., UK. Suitable derivatives include those that are disclosed in Roberts, *Chitin Chemistry*, MacMillan Press Ltd., London (1992).

Particularly preferred chitosan compounds that may be mentioned include chitosan glutamate (available as Protasan UPG213 from NovaMatrix, Drammen, Norway).

The concentration of chitosan in the aqueous solutions is preferably about 0.5 to 50 mg/ml, more preferably about 0.75 to 35 mg/ml and most preferably about 1 to 20 mg/ml.

A preferred chitosan-containing aqueous solution of the invention comprises about 1 to 112 mg/ml (for example about 6 to 60 mg/ml) of granisetron hydrochloride and about 2 to 10 mg/ml of chitosan glutamate.

The chitosan-containing aqueous solutions preferably have an osmolality within the ranges set out above. The agents mentioned above for adjusting the osmolality of the aqueous solutions can be used to adjust the osmolality of chitosan containing solution.

The aqueous solutions containing chitosan, a salt or derivative thereof or a salt of a chitosan derivative preferably have a pH of about 3 to 6, more preferably about 3.5 to 5.8 and most preferably about 4.0 to 5.6. The pH of the chitosan-containing solutions may be adjusted as described earlier although it is preferred not to use citrate salts as the use of citrate salts can result in precipitate formation in the presence of chitosan.

Surprisingly, the present inventors have found that the use of chitosan, a salt or derivative thereof or a salt of a derivative of chitosan increases the rate of intranasal absorption of granisetron. By "increased rate of absorption", we mean that the time after administration to reach the maximum plasma concentration ($T_{max}$) is shorter compared to a composition that contains no chitosan. A shorter $T_{max}$ should equate to a more rapid onset of action.

The water used to prepare the solutions of the present invention can be boiled and cooled and/or purged with a gas, such as helium, in order to minimize the dissolved oxygen content and hence maximize drug stability. Purified water, such as water for injections, may be used in the compositions of the present invention.

The compositions of the invention may, alternatively, be in the form of a non-aqueous solution or a powder composition.

Solvents that may be used to prepare the non-aqueous solutions of the invention include, but are not limited to ethanol, propylene glycol, polyethylene glycol, glycofurol, benzyl benzoate and polyoxyethylene castor oil derivatives, such as Cremophor® (BASF, Germany). The concentration of granisetron or a salt thereof in the non-aqueous solutions of the invention is typically as described above for the aqueous solutions. The viscosity of the non-aqueous solutions of the invention is typically as described above for the aqueous solutions.

The solutions of the invention may also contain thickening, adhesive or gelling agents, such as, but not limited to, celluloses (e.g. hydroxypropyl methylcellulose, methylcellulose, hydroxypropyl cellulose and microcrystalline cellulose), carbomers, polyethylene oxide, poloxamers or polyethylene glycols.

The solutions of the present invention may also contain other pharmaceutically acceptable ingredients well known in the art. Such ingredients include, but are not limited to, antioxidants (for example sodium metabisulphite), chelating agents (such as edetic acid or one of its salts), preservatives (such as potassium sorbate, parabens, phenylethyl alcohol or benzalkonium chloride), flavors and sweeteners.

Preferably the solutions of the invention contain a preservative and/or are sterile. If preservatives are omitted from the compositions, microorganisms may be removed using any suitable method known in the art, for example by making the compositions aseptically or by terminally sterilizing them.

Preferably the compositions of the invention are non-pyrogenic.

Methods of formulating drug substances for administration in a powder form are well known to those skilled in the art. For example, the powder formulations of the present invention may be in the form of a blend of drug powder with other ingredients, or in the form of granules or microspheres.

A powder blend according to the present invention may be prepared by mixing granisetron or a pharmaceutically acceptable salt thereof with inert ingredients that are standard in the art. Such inert ingredients include, but are not limited to, diluents such as calcium phosphate, lactose, sugars such as sucrose and dextrose, polyols such as mannitol and sorbitol, and microcrystalline cellulose, glidants such as colloidal silica, lubricants such as magnesium stearate and hydrogenated vegetable oil and surfactants such as polysorbates; and polyethylene glycol. The powder blend may optionally contain chitosan, a salt or derivative of chitosan or a salt of a derivative of chitosan.

For preparing a uniform powder blend on a small scale, a pestle and mortar and/or sieve may be appropriate whereas mechanical mixers are required for larger scale manufacture. There are numerous types of mixer available and these are widely described in the literature, for example Chapter 37, Remington: *The Science and Practice of Pharmacy*, 20$^{th}$ Edition, Lipincott, Williams and Wilkins, Baltimore (2000).

Alternative processes for preparing the formulations of the invention include spray drying, granulation and supercritical fluid processes.

If the powder composition of the invention comprises granules, these granules may be produced by techniques well known to those skilled in the art such as wet granulation, dry granulation (slugging), extrusion/spheronization, fluid bed granulation and spray congealing. Further details on granulation processes may be found in the literature, for example Chapter 6, *Pharmaceutical Principles of Solid Dosage Forms*, J. T. Carstensen, Technomic, Lancaster, Pa. (1993).

In addition to granisetron or a pharmaceutically acceptable salt thereof, other ingredients may be incorporated into the granules. Such other ingredients include, but are not limited to, starches, diluents such as calcium phosphate, lactose, dextrose, mannitol and celluloses such as microcrystalline cellulose, binders such as povidone (polyvinylpyrrolidone), methylcellulose, polyethylene glycol, gelatin and acacia, disintegrants such as starch, croscarmellose and crospovidone, glidants such as colloidal silica, and lubricants such as magnesium stearate and hydrogenated vegetable oil. The granules may optionally contain chitosan, a salt or derivative of chitosan or a salt of a derivative of chitosan.

Methods for preparation of microspheres are well known to those skilled in the art and include, but are not limited to, spray drying, interfacial polymerisation, coarcervation/phase separation and solvent evaporation. Methods for producing microspheres are described in, for example, *Physicochemical Principles of Pharmacy*, 3$^{rd}$ Edition, pages 357 to 360, A T Florence and D Attwood, Macmillan, London (1998) and *Physical Pharmacy*, 4$^{th}$ Edition, pages 516 to 519, A Martin, Wilkins and Wilkins, Baltimore (1993). The microspheres may alternatively be produced using the methods described in International patent application publication WO98/30207 and the documents cited therein.

In addition to granisetron or a pharmaceutically acceptable salt thereof, the microspheres used in the present invention may include ingredients that are known in the art to be suitable to be included in microspheres such as, but not limited to, starches, dextrans, gelatin, albumin, collagen, hyaluronic acid, chitosan, lactose, sucrose, dextrose, mannitol, methacrylate copolymers such as the Eudragit® polymers (Degussa, Germany), celluloses such as methylcellulose, and polyesters such as poly(lactide-co-glycolide).

The powder formulations of the present invention preferably have a granisetron content of about 2 to 90% by weight (calculated as the free base) of the formulation, more preferably about 5 to 70% by weight and most preferably about 10 to 50% by weight.

If the powder formulations of the present invention comprise chitosan, a salt or derivative of chitosan or a salt of a derivative of chitosan, they preferably have a chitosan content of about 2 to 95% by weight (calculated as the free base) of the formulation, more preferably about 5 to 90% by weight and most preferably about 10 to 80% by weight.

The powder formulations of the invention preferably have a particle size in the range of about 10 to 900 µm, more preferably about 10 to 600 µm and most preferably about 10 to 300 µm. More specifically, the mean particle size, expressed as the volume mean diameter ($D_{50\%}$) and measured by a technique, such as light microscopy combined with image analysis, lies within these ranges. The $D_{50\%}$ is preferably about 25 to 700 µm, more preferably about 25 to 450 µm and most preferably about 25 to 200 µm. Furthermore, no more than about 10% by volume of the particles has a diameter ($D_{10\%}$) less than about 10 µm and at least about 90% by volume of the particles has a diameter ($D_{90\%}$) that does not exceed the upper limit of the size range.

It is desirable that the formulations of the invention do not contain substantial numbers of particles having a size below about 10 µm in order to minimize the possibility of delivery into the lungs.

The compositions of the invention may include another drug in addition to granisetron or a pharmaceutically acceptable salt thereof. Any appropriate and compatible additional drug may be used. Preferred additional drugs include antiemetic corticosteroids, such as dexamethasone or a pharmaceutically salt or ester thereof.

The compositions of the invention may be administered to the nasal cavity in any suitable form. For example, the solutions of the invention may be administered to the nasal cavity in the form of drops or a spray and the powders of the invention may be administered in aerosolized form.

A preferred method of administering the solutions of the invention is using a spray device. Spray devices can be single ("unit") dose or multiple dose systems, for example comprising a bottle, pump and actuator, and are available from various commercial sources, including Pfeiffer (Germany), Valois (France), Calmar (Germany), Ursatech (Germany), Bespak (UK) and Becton-Dickinson (USA). Electrostatic spray devices, such as described in U.S. Pat. No. 5,655,517, are also suitable for the intranasal administration of the solutions of the invention.

For a spray device, the typical volume of liquid that is dispensed in a single spray actuation is about 0.01 to 0.14 ml, for example about 0.05 to 0.14 ml, such as 0.1 ml. It is a practical proposition to administer up to about 0.2 ml into each nostril (i.e. two×0.1 ml sprays) to provide a therapeutic dose of drug, although the most acceptable dosing regimen would be one spray into one or both nostrils. On the basis of administering a granisetron dose of 2 mg (expressed as free base) as a total of one or two 0.1 ml sprays, the drug concentration is preferably about 11 to about 22 mg/ml granisetron hydrochloride. Obviously, smaller spray volumes (or larger drug doses) could be administered if there were a corresponding increase in drug concentration, e.g., a 2 mg dose could be administered as a single 0.05 ml spray of a 45 mg/ml granisetron hydrochloride solution.

The powder formulations of the present invention are preferably administered to the patient in aerosolized form whereby energy from patient inhalation (sniffing) is used to aerosolize the powder into the nasal cavity or where the device itself provides the aerosolization energy, such as via compressed air. An example of the former device is manufactured by Pfeiffer and an example of the latter is the "Monopowder" manufactured by Valois.

The present invention also provides a nasal drug delivery device or a dose cartridge for use in a nasal delivery device loaded with a composition as defined above.

The present invention also provides processes for preparing the compositions of the invention. The process for preparing the solutions of the invention comprises mixing the components in a suitable solvent such as water. The powder compositions may be prepared using methods known in the art.

The compositions of the present invention have antiemetic properties and may be used in the treatment and/or prevention of nausea and/or vomiting, in particular arising during cancer chemotherapy, radiotherapy and following surgery. Thus, the present invention provides a method of administering granisetron to a patient in need thereof, for example for the prevention or treatment of the conditions set out above, which comprises the intranasal administration of a composition as defined above to the patient.

The present invention also provides the use of granisetron or a salt thereof in manufacture of a medicament for nasal administration to a patient in need thereof. Such a medicament may have antiemetic properties and may be used in the treatment and/or prevention of nausea and/or vomiting.

The invention is illustrated by the following non-limiting examples.

Example 1

Intranasal Solution Containing 20 mg/ml Granisetron 4.468 g of granisetron hydrochloride (ZMC, Hangzhou, China) was weighed into a 100 ml volumetric flask and 90 ml of water for injection (Baxter, Thetford, UK) was added. The flask contents were stirred until the drug had dissolved and then made to volume with water. This produced a stock solution containing 40 mg/ml granisetron (base).

40 mg of sodium hydroxide (Fisher, Loughborough, UK) was weighed into a 100 ml volumetric flask and 90 ml of water for injection added. The flask contents were stirred until the sodium hydroxide had dissolved and then made to volume with water. This produced 0.01M sodium hydroxide solution.

300 mg of 50% benzalkonium chloride solution (Albright & Wilson, Whitehaven, UK) was weighed into a 10 ml volumetric flask and 8 ml of water for injection added. The flask contents were stirred to disperse the benzalkonium chloride and then made up to volume with water. This produced a stock solution containing 15 mg/ml benzalkonium chloride.

Using a pipette, 12.5 ml of the 40 mg/ml granisetron stock solution was dispensed into a 25 ml volumetric flask. 8 ml of water for injection and 0.25 ml of 15 mg/ml benzalkonium chloride solution were added to the flask. 170 mg of sodium chloride (Sigma, Poole, UK) was added to the flask and stirred until dissolved. The pH of the solution was adjusted to 5.0 by adding 0.01M sodium hydroxide solution. The flask contents were made up to volume with water. The final pH was 5.25 and the osmolality was 0.304 osmol/kg. The solution was analyzed by HPLC for granisetron content. The assayed content was 20.2 mg/ml.

Example 2

Intanasal Solution 20 mg/ml Granisetron and 5 mg/ml Chitosan Glutamate 250 mg of chitosan glutamate (Protasan UPG213, NovaMatrix, Drammen, Norway) was weighed into a 50 ml volumetric flask. 25 ml of 40 mg/ml granisetron stock solution (prepared in Example 1) and 15 ml of water for injection were added to the flask. The flask contents were stirred until the chitosan had dissolved. 0.5 ml of 15 mg/ml benzalkonium chloride stock solution (Example 1) and 0.327 g of sodium chloride were added to the flask containing chitosan and granisetron and the contents stirred until dissolved. The flask contents were made up to volume with water and the pH, osmolality and granisetron content (HPLC) measured. The pH was 4.85, the osmolality was 0.303 osmol/kg and the granisetron content was 20.0 mg/ml.

Example 3

Pharmacokinetic Performance of Intranasal Granisetron Formulations in Sheep

The pharmacokinetic performance of the intranasal granisetron solutions described in Examples 1 and 2 was evaluated in sheep. For purposes of determining the absolute bioavailability of the intranasal doses, an intravenous injection of granisetron was administered. The injection product contained 1 mg/ml granisetron (Kytril® injection, Roche, Welwyn, UK).

A group of five female sheep was used, each weighing around 35 kg. The formulations were administered to a randomized cross-over design. Each intranasal formulation was administered at a granisetron dose of 8 mg. This dose was provided by administering 0.4 ml of each formulation via a spray device with the dose volume being divided equally between both nostrils. The formulations were well tolerated by the sheep, as measured by the frequency of snorting and sneezing post-dose. For the intravenous dose, 2 ml of Kytril® injection (i.e. 2 mg of granisetron) was administered as a bolus injection.

Blood samples were collected over a 360 minute period following dosing and plasma separated. Granisetron was isolated from the plasma samples by solid phase extraction and quantified by an HPLC method (fluorescence detection). Pharmacokinetic parameters were calculated from the plasma data.

A summary of pharmacokinetic parameters is provided in Table 1. Plasma concentration versus time curves are provided in FIG. 1.

TABLE 1

Summary of pharmacokinetic parameters following administration of granisetron intranasal and IV injection doses to sheep (mean, n = 5 [SD]).

| Dose group | $T_{max}$ (min) | $C_{max}$ (ng/ml) | Absolute bioavailability (%) |
|---|---|---|---|
| Nasal solution (Example 1) | 14 [2] | 19 [4] | 48 [8] |
| Nasal solution + 5 mg/ml chitosan (Example 2) | 8 [3] | 26 [4] | 50 [12] |
| IV injection (Kytril ®) | 0 [0] | 54 [15] | 100 |

Granisetron was well absorbed by the intranasal route in sheep, with a bioavailability relative to intravenous injection of around 50%. The peak plasma concentration ($C_{max}$) was higher for the chitosan-containing solution and was reached more rapidly ($T_{max}$) Statistically $T_{max}$ was significantly different ($p<0.05$) between the two nasal dose groups.

Example 4

Intranasal Solution Containing 50 mg/ml Granisetron 279.3 mg of granisetron hydrochloride (=250 mg granisetron base) was weighed into a 5 ml volumetric flask and 4 ml of water added. The flask contents were stirred until the drug had dissolved. 17.5 mg of sodium chloride (Sigma), 1 mg of propyl parabens (Nipa Laboratories, UK) and 25 µl of phenylethyl alcohol (R. C. Treatt, UK) were added to the granisetron solution and the flask contents stirred until all of the ingredients had dissolved. 160 µl of 0.01M sodium hydroxide solution was added to the flask and the contents made to volume with water. The final solution had a pH of 5.5 and had an osmolality of 0.344 osmol/kg.

Example 5

Intranasal Solution Containing 20 mg/ml Granisetron in pH 5 Buffer 0.9073 g of potassium dihydrogen orthophosphate (BDH, UK) was dissolved in approximately 90 ml of water and then made up to 100 ml in a volumetric flask (Solution A). 0.2374 g of disodium hydrogen orthophosphate (Fisher, UK) was dissolved in approximately 15 ml of water and then made up to 20 ml in a volumetric flask (Solution B).

49.6 ml of Solution A was dispensed into a 50 ml volumetric flask and the flask contents made up to 50 ml using Solution B (=Solution C).

112 mg of granisetron hydrochloride (=100 mg granisetron base) was weighed into a 5 ml volumetric flask and dissolved in 4 ml of Solution C. 9.3 mg of sodium chloride and 7.5 mg of potassium sorbate (Sigma) were dissolved in the granisetron solution and the flask contents made up to volume with Solution C. The final solution had a pH of 5.1 and had an osmolality of 0.28 osmol/kg.

Example 6

Intranasal Solution Containing 10 mg/ml Granisetron in pH 6 Buffer 44.5 ml of Solution A (Example 5) was dispensed into a 50 ml volumetric flask and the flask contents made up to 50 ml using Solution B (Example 5) (=Solution D).

55.9 mg of granisetron hydrochloride (=50 mg granisetron base) was weighed into a 5 ml volumetric flask and dissolved in 4 ml of Solution D. 95 mg of mannitol (Roquette, France) and 50 µl of 15 mg/ml benzalkonium chloride solution (Example 1) were dissolved in the granisetron solution and the flask contents made up to volume with Solution D. The final solution had a pH of 5.9 and had an osmolality of 0.29 osmol/kg.

Example 7

Powder Blend Comprising Granisetron Hydrochloride and Chitosan Glutamate 2.24 g of granisetron hydrochloride, 5 g of chitosan glutamate (Protasan UPG213, NovaMatrix, Norway) and 2.76 g of lactose (InhaLac® 120, Meggle, Germany) are weighed into a glass bottle. A lid is attached to the bottle, which is placed into a Turbula T2C mixer (Willy Bachofen, Basel, Switzerland). The bottle contents are mixed at speed setting 2 for 30 minutes. A 10 mg sample of the powder blend is filled into a Monopowder nasal spray device (Valois, Marly-le-Roi, France). When actuated, this device will deliver 10 mg of powder, equivalent to 2 mg of granisetron.

Example 8

20 mg/ml Granisetron Solution in pH 5 Citric Acid/Sodium Phosphate Buffer 0.210 g citric acid (Fisher Scientific, Loughborough, UK) was dissolved in approximately 9 ml of water and then made up to 10 ml in a volumetric flask to produce Solution 1.

0.356 g of disodium hydrogen orthophosphate dihydrate (Fisher Scientific) was dissolved in approximately 9 ml of water and then made up to 10 ml in a volumetric flask to produce Solution 2.

Into a 10 ml volumetric flask was dispensed 5 ml of Solution 1 and the flask contents made up to 10 ml using Solution 2 to produce Solution 3.

0.224 g granisetron hydrochloride (Hisun, Zhejiang, China) was dissolved in approximately 4 ml of water and then made up with water to 5 ml in a volumetric flask. This produced a stock solution containing 40 mg/ml granisetron (base).

Using a pipette, 2.5 ml of the 40 mg/ml granisetron stock solution was dispensed into a 5 ml volumetric flask. 1.5 ml of Solution 3 and 0.05 ml of 15 mg/ml benzalkonium chloride solution were added to the flask. 7.7 mg of sodium chloride (Mallinckrodt, USA) was added to the flask and stirred until dissolved. The flask contents were then made up to volume with Solution 3. The final pH was 4.93 and the osmolality was 0.293 osmol/kg.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of administering granisetron or a pharmaceutically acceptable salt thereof to a patient in need thereof, which method comprises intranasally administering a composition in the form of an aqueous solution for intranasal administration consisting essentially of granisetron or a pharmaceutically acceptable salt thereof, chitosan, a salt or a derivative thereof, wherein the derivative is selected from an ester, ether or other derivative of chitosan formed by bonding at least one of an acyl and an alkyl group with at least one of the hydroxyl groups, but not the amino groups of chitosan, and optionally, at least one osmolality adjusting agent, and wherein the chitosan, the salt or a derivative thereof is present in an amount sufficient to provide a time to maximum plasma concentration ($T_{max}$) of granisetron or a pharmaceutically acceptable salt thereof shorter than the $T_{max}$ for the granisetron or a pharmaceutically acceptable salt thereof in a corresponding composition not including the chitosan, salt or a derivative thereof.

2. The method according to claim 1, wherein the granisetron or a pharmaceutically acceptable salt thereof is at least one salt of granisetron selected from the group consisting of hydrochloride, mesilate, citrate, nitrate, lactate, maleate, tartrate, phosphate, succinate, fumarate and gluconate salts.

3. The method according to claim 2, wherein the granisetron salt is the hydrochloride salt.

4. The method according to claim 1, wherein the granisetron or a pharmaceutically acceptable salt thereof is present in an amount of about 0.2 to 150 mg/ml of granisetron, expressed as the free base.

5. The method according to claim 4, wherein the granisetron or a pharmaceutically acceptable salt thereof is present in an amount of about 1 to 100 mg/ml of granisetron, expressed as the free base.

6. The method according to claim 1, wherein the composition has an osmolality of about 0.15 to 0.45 osmol/kg.

7. The method according to claim 1, wherein the composition has a pH of about 4 to 7.

8. The method according to claim 1, wherein the chitosan, a salt or a derivative thereof is present in an amount of about 0.5 to 50 mg/ml of chitosan.

9. The method according to claim 1, wherein the composition consists essentially of about 1 to 112 mg/ml of granisetron hydrochloride and 2 to 10 mg/ml of chitosan glutamate, and optionally, at least one osmolality adjusting agent.

10. The method of claim 1, wherein the method is a method of treating or preventing nausea and/or vomiting.

11. The method of claim 1, wherein the granisetron or a pharmaceutically acceptable salt thereof is present in an amount of about 0.5 to 125 mg/ml of granisetron, expressed as the free base.

12. The method of claim 1, wherein the granisetron or a pharmaceutically acceptable salt thereof is present in an amount of about 5 to 100 mg/ml of granisetron, expressed as the free base.

13. The method of claim 1, wherein the granisetron or a pharmaceutically acceptable salt thereof is present in an amount of about 6 to 60 mg/ml of granisetron hydrochloride.

14. The method of claim 1, wherein the chitosan, a salt or a derivative thereof is present in an amount of about 0.75 to 35 mg/ml of chitosan.

15. The method of claim 1, wherein the chitosan, a salt or a derivative thereof is present in an amount of about 1 to 20 mg/ml of chitosan.

16. The method of claim 1, wherein the chitosan salt is selected from the group consisting of nitrate, phosphate, glutamate, lactate, citrate and hydrochloride and acetate salts of chitosan.

17. The method of claim 16, wherein the chitosan salt is chitosan glutamate.

18. The method of claim 1, wherein the at least one osmolality adjusting agent, when present, is at least one of a polyol, a sugar or a salt.

19. The method of claim 18, wherein when the at least one osmolality adjusting agent is present, the osmolality adjusting agent is mannitol or sorbitol.

20. The method of claim 19, wherein when the at least one osmolality adjusting agent is present, the osmolality adjusting agent is mannitol.

21. The method of claim 18, wherein when the at least one osmolality adjusting agent is present, the osmolality adjusting agent is dextrose.

22. The method of claim 18, wherein when the at least one osmolality adjusting agent is present, the osmolality adjusting agent is sodium chloride.

23. The method of claim 1, wherein the composition has an osmolality of about 0.20 to 0.40 osmol/kg.

24. The method of claim 6, wherein the composition has an osmolality of about 0.25 to 0.35 osmol/kg.

* * * * *